(12) United States Patent
Samples et al.

(10) Patent No.: US 7,249,497 B2
(45) Date of Patent: Jul. 31, 2007

(54) APPARATUS AND METHOD FOR PREDICTING TIRE LIFE RELATIVE TO BELT-LEAVES-BELT FAILURES

(75) Inventors: C. Robert Samples, Akron, OH (US); Blake E. Matthies, Akron, OH (US); Walter B. Samples, Akron, OH (US); Uday Prakash Karmarker, Akron, OH (US)

(73) Assignee: Akron Rubber Development Laboratory, Inc., Akron, OH (US)

( * ) Notice: Subject to any disclaimer, the term of this patent is extended or adjusted under 35 U.S.C. 154(b) by 0 days.

(21) Appl. No.: 10/896,767

(22) Filed: Jul. 21, 2004

(65) Prior Publication Data

US 2005/0061068 A1    Mar. 24, 2005

Related U.S. Application Data

(60) Provisional application No. 60/488,922, filed on Jul. 21, 2003.

(51) Int. Cl.
*G01M 17/02* (2006.01)
(52) U.S. Cl. ...................................... 73/146
(58) Field of Classification Search .............. 73/146; 265/501, 502
See application file for complete search history.

(56) References Cited

U.S. PATENT DOCUMENTS

| | | |
|---|---|---|
| 2,345,679 A | 4/1944 | Linse |
| 3,316,758 A | 5/1967 | Wild |
| 3,554,027 A | 1/1971 | Sperberg |
| 3,563,088 A | 2/1971 | Sperberg |
| 3,894,421 A | 7/1975 | Sperberg |
| 4,938,056 A | 7/1990 | DeRudder et al. |
| 5,067,347 A | 11/1991 | Mönch |
| 6,119,513 A | 9/2000 | Tanaka |
| 6,203,748 B1 * | 3/2001 | Kumagai .................. 264/502 |
| 6,740,280 B1 * | 5/2004 | Brown et al. ............ 264/326 |

FOREIGN PATENT DOCUMENTS

JP    64 32142 A    2/1989

* cited by examiner

*Primary Examiner*—Edward Lefkowitz
*Assistant Examiner*—Andre Allen
(74) *Attorney, Agent, or Firm*—Hahn Loeser & Parks, LLP; Robert J. Clark (57) ABSTRACT

A test fixture, test apparatus, and test method utilize a radially cut tire section that is mounted and sealed to a test jig in a airtight manner such that an air chamber is formed between an innerliner surface of the radial tire section and a recessed portion of the jig body such that the tire section may be pressurized on the test jig. A test surface is provided and either the test surface or the test jig is moveable relative to the other to the other to provide a dynamic load to the radial tire sections.

10 Claims, 7 Drawing Sheets

APPARATUS AND METHOD FOR PREDICTING TIRE LIFE RELATIVE TO BELT-LEAVES-BELT FAILURES

This application claims the benefit of U.S. provisional patent application Ser. No. 60/488,922, filed Jul. 21, 2003, and is hereby incorporated by reference.

TECHNICAL FIELD

The present invention relates to an apparatus for conducting a predictive test to determine failure due to "belt-leaves-belt" ("BLB") separations in a tire, particularly a radial passenger automobile tire.

BACKGROUND OF THE ART

In a "belt-leaves-belt" failure, particularly involving a steel-belted radial tire, the adjacent belts in the tire separate from each other. These tire failures may occur from a variety of problems, but regardless of the problem, it is essential that a tire manufacturer be able to effectively test tires to predict such failures.

The BLB failure appears to be exemplified by a premature aging or oxidation, so it may be predicted by accelerating the aging process, by exposing the tire to increased temperature or oxygen partial pressure while exposing the tire to a dynamic vibratory input that dynamically activates the process of thermal and oxidative aging simulating dynamic road conditions.

In some of the known prior art methods, a series of complete tires are tested at differing time, temperature and oxygen pressure schemes. An inherent difficulty with this methodology is that variations in the individual tires used confounds the testing methodology, resulting in unacceptable data scatter. This data scatter can be eliminated only by exposing the same tire to the differing test conditions, but this is also confounded by the destructive nature of the testing.

It is therefore an object of the present invention to provide a method and device wherein each single complete tire can be used to provide a series of data points, such that individual tire-to-tire variation may be demonstrated by comparing the sets of data points generated by the given individual tires.

SUMMARY OF THE INVENTION

This and other objects of the present invention are provided by the apparatus and method for predicting tire life relative to "belt-leaves-belt" failures as described in more detail below.

In the test method of the present invention, a tire to be tested is sectioned into a plurality of identical radial wedges. The radially cut tire section is mounted on a test jig and sealed around its edges to prevent the pressurized air from leaking. The interior chamber of the mounted tire section is then "inflated" such that the interior face of the section is exposed to a higher pressure than the exterior face. This allows diffusion of gas through the tire, simulating an inflated tire. Gas pressure and particularly partial pressure of oxygen at the interior face is controlled in the jig. The exposed exterior face, that is, the tread surface, is exposed to a vibration source, especially a source vibrating at about 10 Hz, to simulate road vibration. If desired, the entire test jig is contained in a temperature controlled chamber, so that increased temperature can be utilized to simulate both operating conditions and to accelerate aging.

BRIEF DESCRIPTION OF THE DRAWINGS

The present invention will be better understood when reference is made to the accompanying drawings, wherein identical parts are identified with identical reference numerals and wherein.

DETAILED DESCRIPTION OF THE PREFERRED EMBODIMENT

The test method of the present invention proceeds from an initial assumption that a statistically significant majority of all steel-belted radial tire failures, excepting those caused by user neglect, road hazard or manufacturing anomalies, are caused by BLB failure, caused in turn by aging of the wedge and skim stocks initiated by the ever-socketing steel belt in the wedge area.

Figure 1:
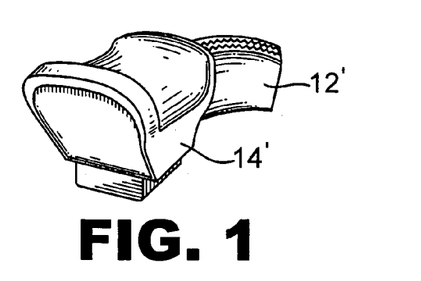
FIG. 1 shows a perspective view of a tire segment and a test jig body as used in one embodiment of the present invention
Figure 2:
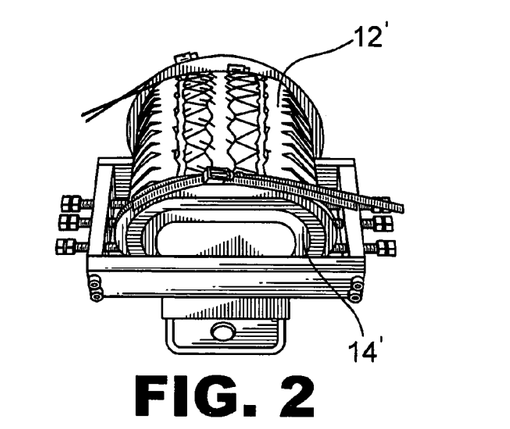
FIG. 2 shows a perspective view of a tire segment mounted on a test jig as used in one embodiment of the present invention.

Referring now to FIG. 1, to test a tire, a single tire is selected and sectioned into suitable circumferential sections 12. The sidewalls are retained and the section is mounted onto the test jig 14 and sealed to prevent air loss as shown in FIG. 2. Two sections 12 are selected for photomicrography prior to testing. In the preferred test, the two sections 12 to be analyzed in this manner should be diametrically opposed in the tire prior to sectioning. In other words, they should be as far apart from each other in the unsectioned tire as possible, to allow the best opportunity to see tire variations. Additionally, the fundamental construction features of the tire sections 12 should be documented, such as component dimensions and placement, gauges of the inner liner, wedge and skim compounds, and stock division lines in the crown and belt regions including tread, tread base, under tread, sidewall, skim and wedge components. These sections may be used as control sections if desired, or other sections may be retained as controls.

Further circumferential sections of the tire are tested in the test jig 20 as described below. These tests are conducted under a simulated inflation, with simulated dynamic vibration, similar tire loads and loading frequency (for example, 1000 pounds and 5 Hz) for various time and temperature combinations. Air permeation rate through the tire section 12 can be measured during the test.

After the testing, the segments 12 will have rubber specimens extracted from the area between the belts. These specimens will be tested to fully characterize them. Tests that would typically be conducted would include: physical properties, for a Ahagon plot; dynamic properties (E", E' and tan delta); sulfidic crosslink densities ($S_P$, $S_D$ and $S_M$); mini or micro DeMattia (for crack growth); antidegradant content (depletion rate); air permeation rate (rate of oxidation); and peel adhesion at both 23 C and 100 C. These tests are itemized for illustrative purposes and additional tests can of course be performed.

Diffusion dependent oxidation, that is, oxidation due to the natural diffusion of oxygen through the tire, is the primary cause of the aging and failure of wedge and the skim stocks. The diffusion rate and the directly related degradation rate are influenced by tire geometry and components. Factors known to be influential include inner liner formulation and gauge and cumulative mechanical flexing.

This testing protocol provides replication as a primary advantage. Prior art methodologies that utilize a series of tires clearly show that differences between tires may be greater than the differences induced in the testing, so the test results are not readily observed. There are several advantages inherent in the simultaneous testing of segments from a single tire. First, tire to tire variations are eliminated. These may include differences in tire builders, difference in curing pressure, and differences in gauges and age of compounds and components. Even day to day variations of a single tire builder can be introduced as a confounding factor when more than one tire is used. Changes in the linkages of sulfur are modified because of oxygen absorption in the tire. While the use of a single tire does not remove variations within a single tire, these variations are effectively recognized by the use of a larger number of segments, rendering outlying samples more obvious.

The economics of using a single tire is also important. By allowing many specimens to be extracted from a single tire, the test jig 14 of the present invention allows the use of experimental designs and other statistical studies. These include factorial or composite designs with replication, Weibull studies and Arrhenius aging studies.

A yet further advantage of the present invention method is that the results would be expected to provide more realistic parameters for finite element analysis studies, which, if permitted, provide even more economical testing through computer simulations. This is particularly useful in determining aerobic/anaerobic aging in a given tire brand.

EXAMPLE 1

ANAEROBIC AGING—In one test, 5-inch circumferential sections were oven-aged prior to preparing test dumbbells. The aging, therefore, is primarily anaerobic and have been exposed to very little oxygen and not at all to an oxygen partial pressure differential across the thickness of the tire section. Thirteen different time and temperature combinations were tested for each tire; the time exposure varying from 0 hrs to 504 hrs and the temperature exposure varying from 60 C to 100 C, as shown below:

| Degrees C. | Time Hours | 0 | 8 | 48 | 96 | 144 | 168 | 336 | 504 |
|---|---|---|---|---|---|---|---|---|---|
| 60 | | | | | X | | X | X | X |
| 80 | | | | | X | X | X | X | |
| 100 | | X | X | X | X | | X | | |

Figure 10:
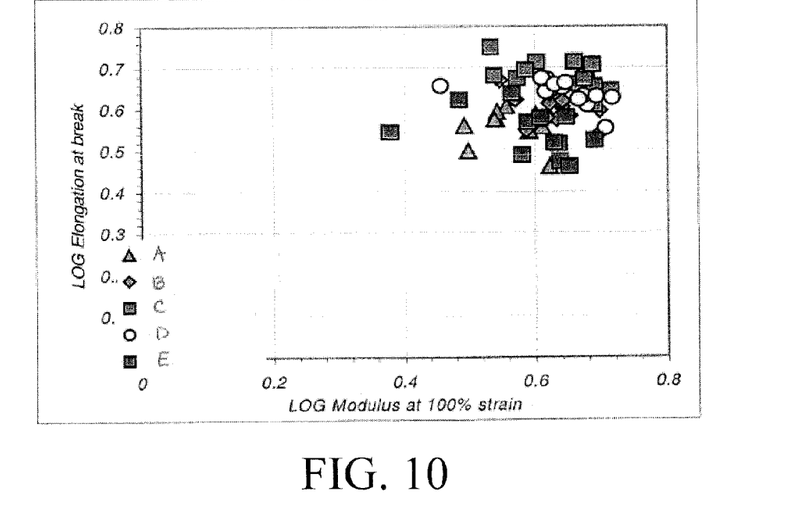
FIG. 10 shows a graph plotting the anaerobic aging results from samples prepared from five different tire manufacturers.

This test varied from an Ahagon aging protocol because the Ahagon test prepares the dumbbells prior to aging and exposes the specimens to more oxygen. The data collected from testing tires from five different tire manufacturers shows a general scatter when log elongation is plotted against log modulus, although manufacturer differences are detectable, as shown in FIG. 10.

EXAMPLE 2

AEROBIC AGING—In this test, dumbbell test samples were prepared from the wedge sections prior to aging. The aging, therefore, was an Ahagon aging, where the dumbbells are exposed to circulating air during aging. Thirteen different time and temperature combinations were tested for each tire; the time exposure varying from 0 hrs to 16 hrs (a 32 fold reduction in time range) and the temperature exposure varying from 60 C to 100 C, as shown in the table below:

Graph 1: Phase I Anaerobic Aging Results.

Figure 11:
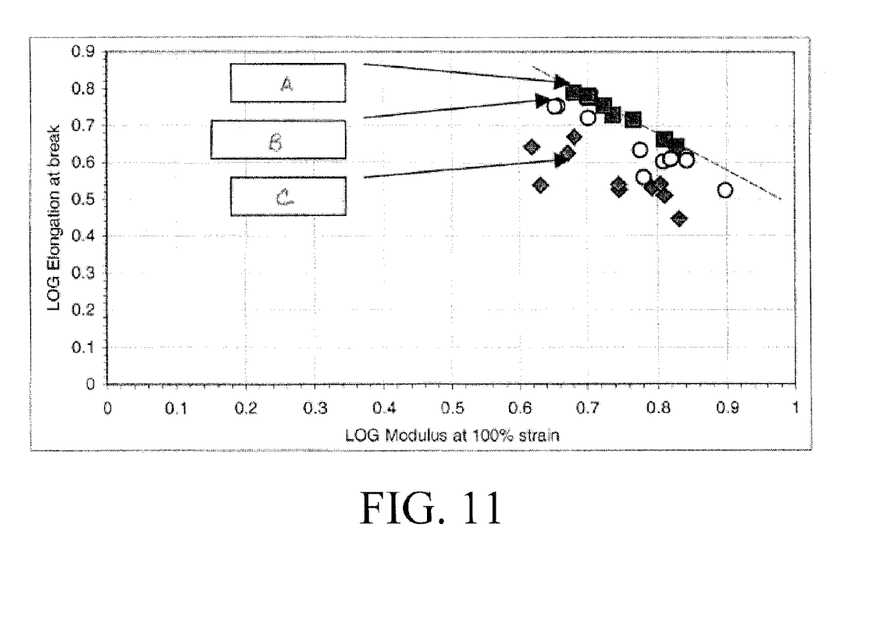
FIG. 11 shows a graph plotting the aerobic aging results from samples prepared from three different tire manufacturers.

The data collected from testing tires from three different tire manufacturers shows a general scatter when log elongation is plotted against log modulus, although manufacturer differences are detectable. The greater linearity of the results is shown in FIG. 11.

EXAMPLE 3 A

Figure 3:
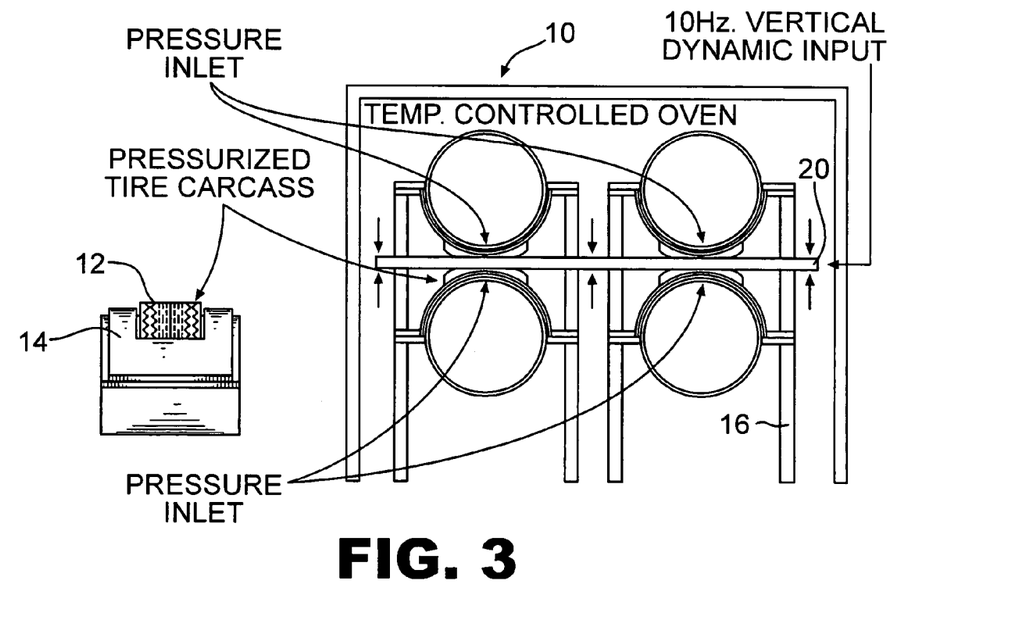
FIG. 3 shows a side view of a first test configuration of the present invention utilizing a plurality of test surfaces and mounted tire segments in accordance with an embodiment of the present invention.
Figure 4:
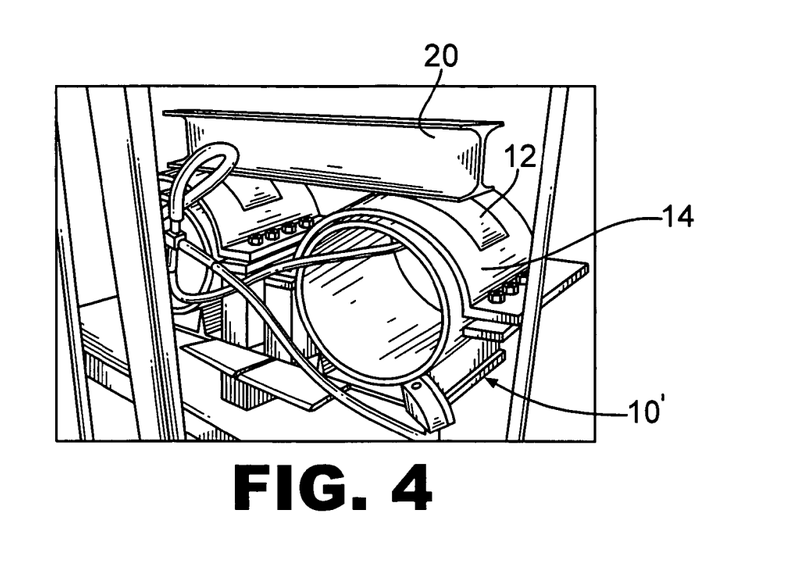
FIG. 4 shows a perspective view of a variation of the first test configuration utilizing two test positions.

In this test, the intent is to provide a realistic "in service" oxygen degradation using the test devices of the present invention, to overcome the perceived weaknesses of the oxygen starved anaerobic method and the excessive oxygen exposure of the Ahagon aging testing. In this example, the intent is to age the tire sections under a 30 psig air pressure applied to the interior face, while applying dynamic vibration. Thirteen different time and temperature combinations were tested for each tire; the time exposure varying from 0 hrs to 504 hrs and the temperature exposure varying from 60 C to 100 C, in the same manner shown in Example 1. In this test, the differences in tire constructions that cause stress and strain in the wedge region due to sidewall deflections are not considered. In the preferred embodiment of the test device 10 for this example, as shown in FIG. 3, a plurality of tire sections 12 are provided and each tire section 12 is constrained between a pair of cylindrical plates 14, with the tread exposed to a dynamic vibration imposed by a test surface 16 in the form of a beam or the like. The test surface 120 is moved vertically to provide a load force F at a predetermined frequency as required by the testing. The entire test fixture is housed within a temperature controlled oven 110. FIG. 3 shows a four position configuration while FIG. 4 shows a similar two position configuration, however the present invention is not intended to be limited to any number of test stations.

EXAMPLE 3B

In this test, a saddle-shaped jig 14' is provided as shown in FIGS. 1 and 2, wherein the jig 14' is shown with and without a mounted tire section 12'. In this test, the preferred test specimen is a ⅙ section of a tire circumference, however, the invention is not intended to be limited to such a length. The jig allows the test section 12' to be supported as if a complete tire was present, while providing a sealed air chamber for pressurizing the tire and to expose the tread surface to dynamic vibration, particularly at 10 Hz. Seven different time and temperature combinations were tested for each tire; the time exposure varying from 0 hrs to 168 hrs and the temperature exposure varying from 70 C to 90 C, as shown below:

| Degrees C. | Time hours | 0 | 16 | 48 | 96 | 168 |
|---|---|---|---|---|---|---|
| 70 |  |  |  | X | X | X |
| 90 |  | X | X | X | X |  |

Figure 6:
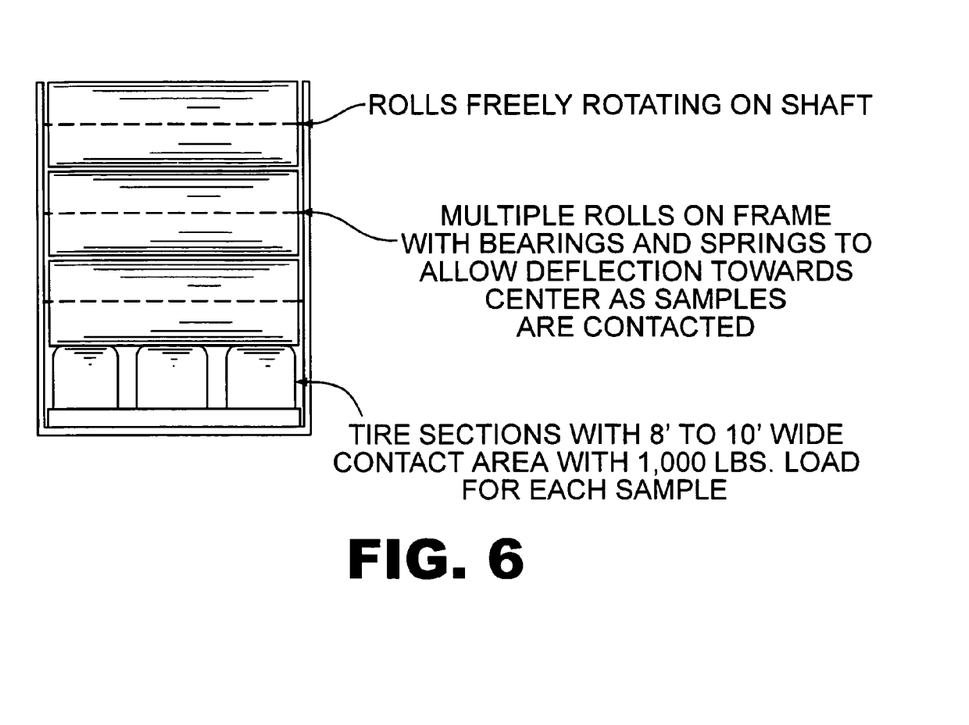
FIG. 6 shows a partial front view of the third test configuration of the present invention as shown in FIG. 5.
Figure 7:
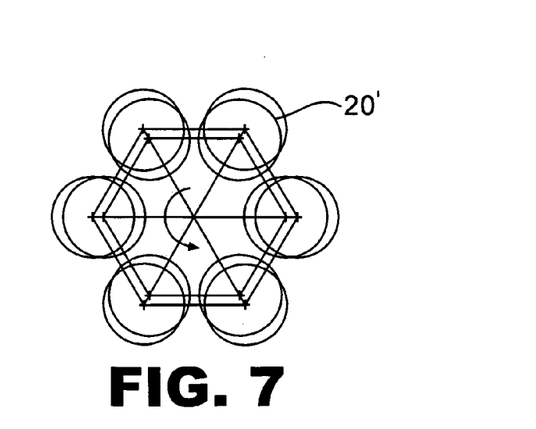
FIG. 7 shows a side view of a the plurality of test surfaces showing the radial displacement of the rollers for loading the tire segments in accordance with an embodiment of the present invention.

In this test, the differences in tire constructions that cause stress and strain in the wedge region due to sidewall deflections are not considered. In the preferred embodiment of the test device 10' for this example, the test jigs can be mounted for exposure on a rotating wheel device that applies the dynamic vibration, as shown in FIGS. 5-7.

Figure 5:
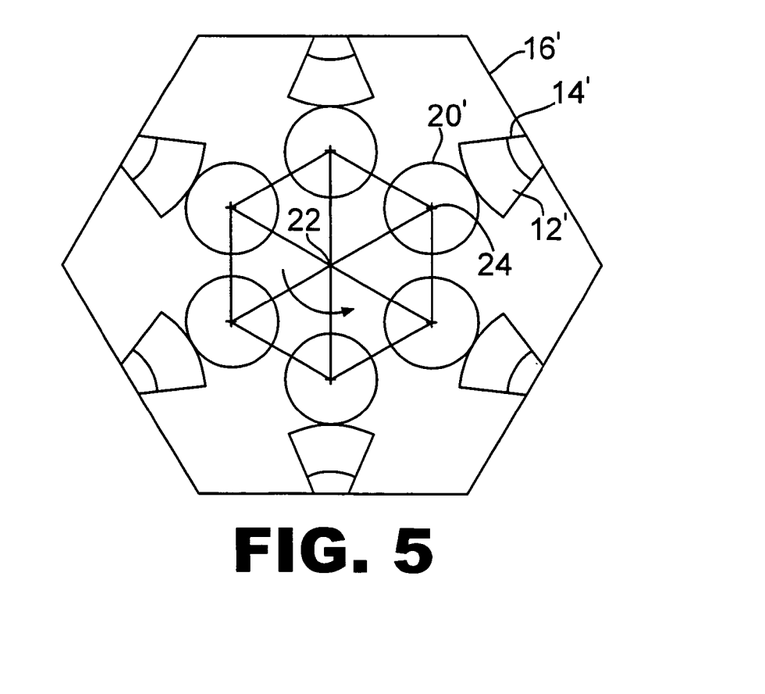
FIG. 5 shows a side view of a third test configuration of the present invention utilizing a plurality of test surfaces and mounted tire segments in accordance with an embodiment of the present invention.

Referring now to FIG. 5, a plurality of radial tire segments 12' are mounted on test jigs 14' and are sealed and pressurized, then mounted on a fixture 16'. A plurality of test surfaces 20' in the form of rolls 20' are shown spaced about a central axis 22. The rolls 20' rotate about axis 22 and engage the stationary tire segments 12'. The roll 20' rotates about its roll axis 24 across the footprint of the tire segment 12'. The roll 20' applies a load force F to the tire segment 12'. The rolls 20' may translate radially inward and outward to apply the appropriate force F as required by the testing as shown in FIG. 7.

Figure 8:
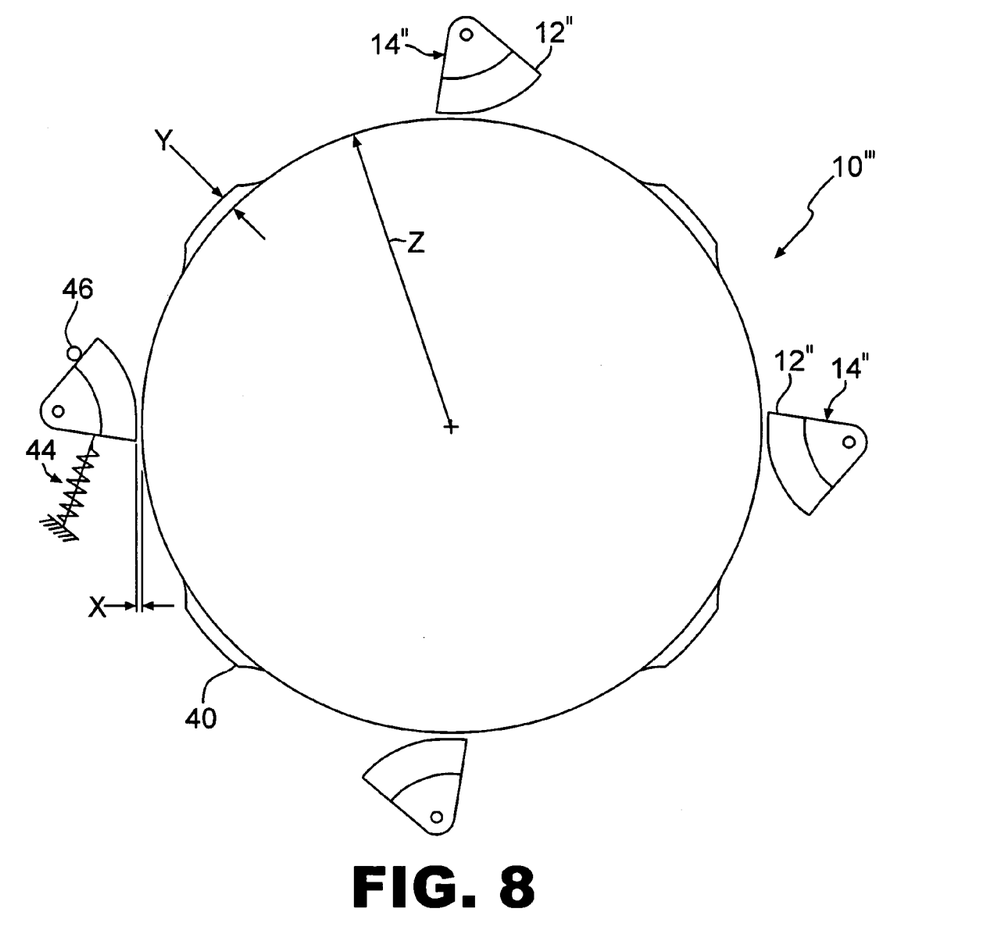
FIG. 8 shows a side view of another test configuration of the present invention.
Figure 9A:
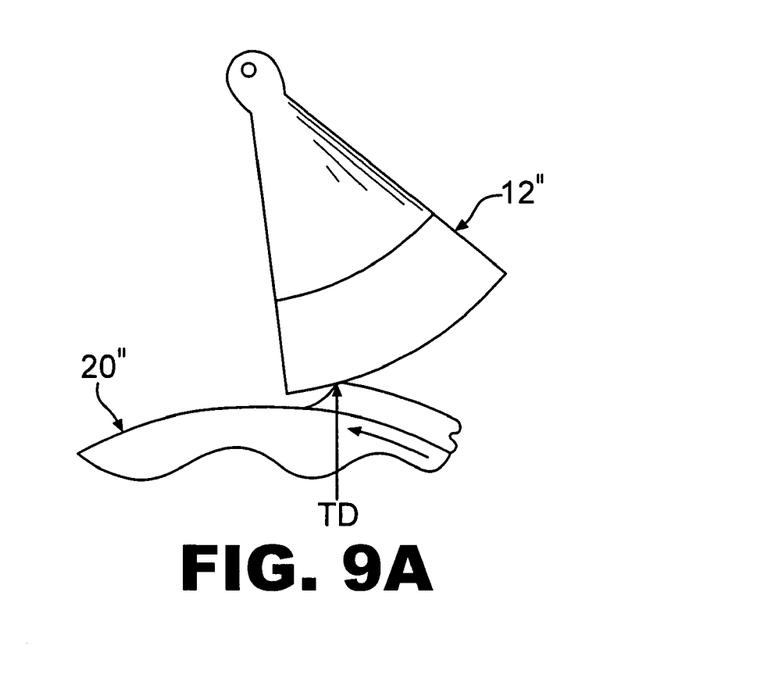
FIGS. 9A-9D show the sequence of tire loading and unloading in the test configuration shown in FIG. 8.
Figure 9B:
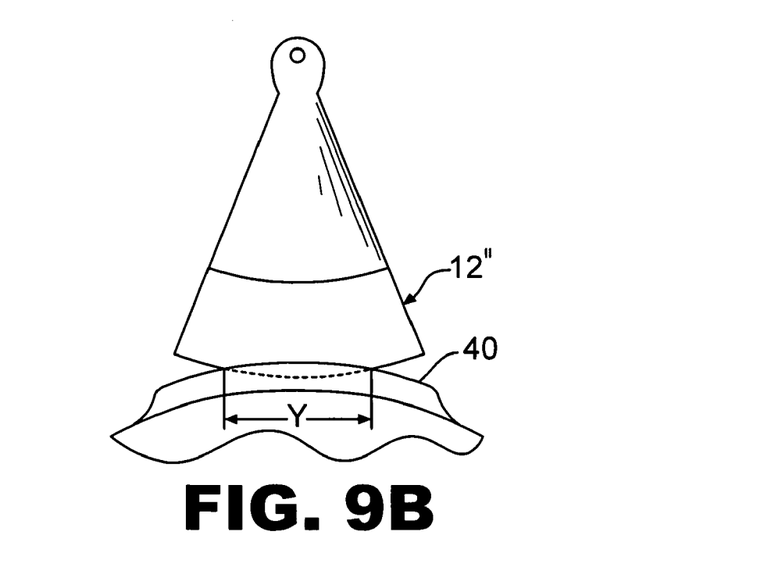
Figure 9C:
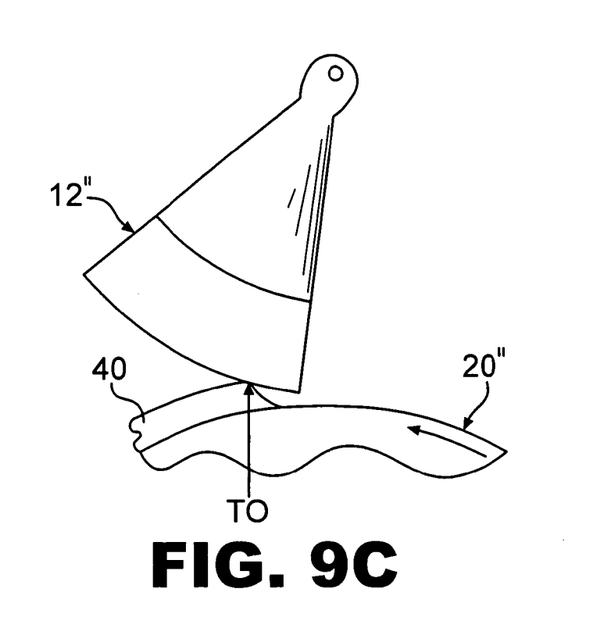
Figure 9D:
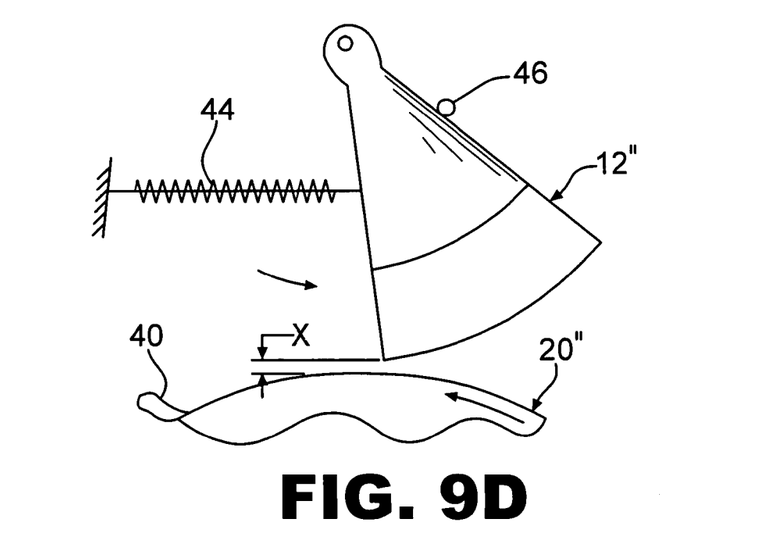

An alternate rolling type of test is also provided by the test configuration 10" as shown in FIGS. 8-9D. FIG. 8 shows a side view similar to that of FIG. 5 except that the test surface 20" is a single drum 20" instead of multiple rollers 20'. The large drum 20" having a radius Z provides less curvature and better simulates the flat road surface. Drum 20" also comprises at least one radial arc portion 40 having a thickness Y, attached thereto and equally spaced about the drum 20". The tire sections 12" are mounted upon a test jig 14" that is pivotal about a central axis 42 of the tire section. As with the previous embodiment, the mounted tire sections 12" are sealed to the jig 14" and pressurized. The tire sections 12" are biased to one side by a biasing means 44 such as a spring or the like and held in a starting position by a stop means 46 (both shown for simplicity on only one station but existing on each station). The operation of the test apparatus 10" is best shown in FIGS. 9A-9D. In FIG. 9A, the tire section 12" is held in position and the drum 20" rotates until an arc portion 40 engages the tire section at a touchdown portion TD. The rotating drum 20" causes the engaged tire section 12" to pivot until the full tire footprint is engaged as best shown in FIG. 9B. The drum 20" continues to rotate and the tire section 12" continues to pivot until the tire section 12" disengages the arc portion 40 at the take off portion TO representing the end of the tire footprint as shown in FIG. 9C. The radius Z of the drum is a distance X away from the tire section 12" so that the drum 20" does not engage the tire section 12" when the arc portion 40 passes the tire section 12". As shown in FIG. 9D, the biasing means 44 is now free to move the tire section 12" back against stop means 46 and to its original start position until it is once again engaged by the next arc portion 40. The distances X and Z are predetermined to provide the appropriate test load and deflection of the tire section at the point of full footprint shown in FIG. 9B. Although shown with only four stations, it is contemplated that six to twelve tire sections may be utilized about the circumference of the drum 20" and the radius of the drum may be any size and is not intended to be limited herein.

It is to be understood, however, that even though numerous characteristics and advantages of the present invention have been set forth in the foregoing description, together with details of the structure and function of the invention, the disclosure is illustrative only, and changes may be made within the principles of the invention to the full extent indicated by the broad general meaning of the terms in which the appended claims are expressed and reasonable equivalents thereof.

The invention claimed is:

1. A tire test apparatus comprising:
   a plurality of radially cut circumferential tire portions cut from at least one tire;
   a plurality of test jigs, each jig comprising a generally saddle-shaped body, the body comprising raised ends on opposite sides of the body and having a recessed portion therebetween;
   wherein each circumferential tire portion is mounted to the test jig and secured to the test jig in an a airtight manner such that an air chamber is formed between an innerliner surface of the circumferential tire portion and the recessed portion of the jig body and that the circumferential tire portion may be pressurized on the test jig;

a test surface;

wherein either the test surface or the test jig is moveable relative to the other to the other to provide a dynamic load to the circumferential tire portions.

2. The apparatus of claim 1, wherein the test surface comprises a plurality of drums.

3. The apparatus of claim 2, wherein the plurality of drums are rotatable about a central axis of the plurality of drums and rotatable about their individual axis.

4. The apparatus of claim 1, wherein the plurality of test jigs are stationary.

5. The apparatus of claim 1, wherein the test surface is a single drum having at least one raised portion on the surface of the drum.

6. The apparatus of claim 1, wherein the test jigs are pivotally moveable.

7. The apparatus of claim 1, wherein the test radial load is provided by a fixed interference distance of overlap between the travel of the test surface and the circumferential tire portion.

8. A tire section test apparatus comprising:

a generally saddle-shaped body, the body comprising raised ends on opposite sides of the body and having a recessed portion therebetween;

a means for removably attaching a circumferential tire section portion cut from a whole tire to the saddle-shaped body in an airtight manner such that the circumferential tire section can be pressurized on the body.

9. A method for testing tires comprising the steps of:

cutting at least one circumferential portion of a tire from at least one tire, mounting the circumferential tire portion on a test jig;

sealing the circumferential tire portion to the test jig to create an air chamber between the circumferential tire portion and the test jig;

pressurizing the assembled circumferential tire portion and test jig;

a means for removably attaching a circumferential tire portion to the body in an airtight manner such that the circumferential tire portion can be pressurized on the jig;

subjecting the circumferential tire portion to a repeated load using a test surface.

10. The method of claim 9, wherein the testing is conducted in an oven chamber.

* * * * *